[US011116877B2](#)

United States Patent
Gifford et al.

(10) Patent No.: US 11,116,877 B2
(45) Date of Patent: Sep. 14, 2021

(54) ANTIBACTERIAL MEDICAL IMPLANT SURFACE

(71) Applicant: INTERNATIONAL BUSINESS MACHINES CORPORATION, Armonk, NY (US)

(72) Inventors: Stacey M. Gifford, Ridgefield, CT (US); Huan Hu, Yorktown Heights, NY (US); Emily R. Kinser, Poughkeepsie, NY (US); Roy R. Yu, Poughkeepsie, NY (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 116 days.

(21) Appl. No.: 15/927,428

(22) Filed: Mar. 21, 2018

(65) Prior Publication Data

US 2018/0272047 A1    Sep. 27, 2018

Related U.S. Application Data

(62) Division of application No. 15/464,386, filed on Mar. 21, 2017, now Pat. No. 10,610,621.

(51) Int. Cl.
| | |
|---|---|
| *A61L 31/16* | (2006.01) |
| *A61L 31/06* | (2006.01) |
| *A61L 31/08* | (2006.01) |
| *B82B 3/00* | (2006.01) |
| *B81C 1/00* | (2006.01) |
| *A61L 27/06* | (2006.01) |
| *A61L 27/30* | (2006.01) |
| *A61L 27/50* | (2006.01) |
| *A61L 27/34* | (2006.01) |
| *A61L 31/10* | (2006.01) |

(52) U.S. Cl.
CPC ............. *A61L 31/16* (2013.01); *A61L 27/06* (2013.01); *A61L 27/306* (2013.01); *A61L 27/34* (2013.01); *A61L 27/50* (2013.01); *A61L 31/06* (2013.01); *A61L 31/088* (2013.01); *A61L 31/10* (2013.01); *B81C 1/00206* (2013.01); *B82B 3/0019* (2013.01); *B82B 3/0033* (2013.01); *A61L 2300/406* (2013.01); *A61L 2300/606* (2013.01); *A61L 2400/12* (2013.01); *A61L 2400/18* (2013.01); *A61L 2420/02* (2013.01); *A61L 2420/08* (2013.01); *B81B 2203/0361* (2013.01); *B81B 2207/056* (2013.01)

(58) Field of Classification Search
CPC ......... A61L 2300/406; A61L 2300/606; A61L 2400/12; A61L 2420/02; A61L 2420/08; A61L 31/06; A61L 31/088; A61L 31/10; A61L 31/16; A61L 2400/18; A61L 27/06; A61L 27/306; A61L 27/34; A61L 27/50; B82B 3/0019; B82B 3/0033; B81B 2203/0361; B81B 2207/056; B81C 1/00206

See application file for complete search history.

(56) References Cited

U.S. PATENT DOCUMENTS

| | | | |
|---|---|---|---|
| 5,863,710 A | 1/1999 | Wakiya et al. | |
| 7,972,616 B2 | 7/2011 | Dubrow et al. | |
| 8,545,559 B2 | 10/2013 | Bandyopadhyay et al. | |
| 9,011,668 B2 | 4/2015 | Speitling | |
| 10,610,621 B2* | 4/2020 | Gifford ................... | A61L 27/34 |
| 2005/0038498 A1* | 2/2005 | Dubrow ................... | A61L 31/14 |
| | | | 623/1.15 |
| 2006/0153815 A1 | 7/2006 | Seyda et al. | |
| 2010/0310775 A1 | 12/2010 | Bedell et al. | |
| 2011/0160869 A1* | 6/2011 | Duch ..................... | C12M 25/06 |
| | | | 623/23.5 |
| 2012/0010599 A1 | 1/2012 | Jin et al. | |
| 2013/0197660 A1 | 8/2013 | Bollati et al. | |
| 2014/0086962 A1 | 3/2014 | Jin et al. | |
| 2015/0273755 A1 | 10/2015 | Yee et al. | |
| 2016/0212989 A1 | 7/2016 | Juodkazis et al. | |
| 2017/0174848 A1* | 6/2017 | Gifford .................. | A01N 25/10 |

FOREIGN PATENT DOCUMENTS

| | | |
|---|---|---|
| CA | 2923305 | 3/2015 |
| CN | 101508419 A | 8/2009 |
| CN | 102793948 A | 11/2012 |
| CN | 104203293 A | 12/2014 |
| WO | 2013162482 A1 | 10/2013 |

OTHER PUBLICATIONS

Mikhael et al., ACS Appl. Mater. Interfaces, 3, pp. 3866-3873. (Year: 2011).*
Hu, Huan, et al. "Bio-inspired silicon nanospikes fabricated by metal-assisted chemical etching for antibacterial surfaces." Applied Physics Letters 111.25 (2017): 253701. (Year: 2017).*
Dickson, Mary Nora, et al. "Nanopatterned polymer surfaces with bactericidal properties." Biointerphases 10.2 (2015): 021010. (Year: 2015).*
List of IBM Patents or Patent Applications Treated as Related; (Appendix P), Filed Mar. 21, 2018, 2 pages.
Stacey M. Gifford, et al., "Antibacterial Medical Implant Surface", U.S. Appl. No. 15/464,386, filed Mar. 21, 2017.

(Continued)

*Primary Examiner* — Abigail Vanhorn
(74) *Attorney, Agent, or Firm* — Cantor Colburn LLP; Kristofer Haggerty

(57) ABSTRACT

Aspects include methods of fabricating antibacterial surfaces for medical implant devices including patterning a photoresist layer on a silicon substrate and etching the silicon to generate a plurality of nanopillars. Aspects also include removing the photoresist layer from the structure and coating the plurality of nanopillars with a biocompatible film. Aspects also include a system for preventing bacterial infection associated with medical implants including a thin silicon film including a plurality of nanopillars.

16 Claims, 7 Drawing Sheets

(56) References Cited

OTHER PUBLICATIONS

Stacey M. Gifford, et al., "Antibacterial Medical Implant Surface", U.S. Appl. No. 15/927,419, filed Mar. 21, 2018.
Stacey M. Gifford, et al., "Antibacterial Medical Implant Surface", U.S. Appl. No. 15/927,443, filed Mar. 21, 2018.
Biggs et al., Nanomedicine, 2010, 6(5), pp. 619-633.
Hu et al., Science, 344(6187), pp. 1005-1009. (Year: 2014).
Mao et al., 2009 IEEE 22nd International Conference on Micro Electro Mechanical Systems, 2009, pp. 677-680.
Notification of Transmittal of the International Search Report and the Written Opinion of the International Searching Authority, or the Declaration; Int'l Appln. No. PCT/IB2018/051437; dated: Jun. 13, 2018; Int'l filing date: Mar. 6, 2018; 9 pages.
Sjostrom et al., "Bacterial Nanospike Surfaces Via Thermal Oxidation of Ti Alloy Substrates," 2015 Elsevier B.V. Materials Letters, pp. 22-26.
VJ et al., IEEE Journal of Selected Topics in Quantum Electronics, 2011, 17(4), pp. 1002-1032.
International Search Report; International Application No. 15/927428; International Filing Date: Mar. 21, 2018; dated Jun. 1, 2021; 13 pages.
M. Bechelany et al. "New Silicon Architectures by Gold-Assisted Chemical Etching." ACS Applied Materials and Interfaces, Mar. 2011. 3866-3873.
VJ. Logeeswaran et al. "A Perspective on Nanowire Photodetectors: Current Status, Future Challenges, and Opportunities". IEEE Journal of Selected Topics in Quantum Electonics, vol. 17, No. 4, Jul./Aug. 2011. 31 Pages.

\* cited by examiner

ANTIBACTERIAL MEDICAL IMPLANT SURFACE

DOMESTIC PRIORITY

This application is a division of U.S. application Ser. No. 15/464,386, filed Mar. 21, 2017, the contents of which are incorporated by reference herein in its entirety.

BACKGROUND

The present invention relates generally to medical implant devices and, more particularly, to bioinspired antibacterial surfaces for medical implant devices.

Bacterial infections associated with medical implants, such as orthopedic and dental implants, present an important challenge. Medical implants can be fabricated from a variety of materials and according to diverse methods. Bacteria can come into contact with medical implants prior to or even during surgical implantation procedures in a variety of manners, for instance, due to incomplete or ineffective sterilization of the medical implant device, contamination from the patient such as the patient's skin, contaminated disinfectants, or contaminants associated with surgical instruments. Films of bacterial cells can form across the surface of medical devices after implantation. The potential for such biofilm-associated infections continuously increases as the world population ages and undergoes more frequent implantation procedures. In many cases, bacterial infections associated with medical implants are first detected in later stages of infection, where surgical intervention is the only option for treating the infection.

Methods to prevent infection associated with implants include alpha radiation and high temperature steam heating. However, these methods can only reduce or eliminate bacteria present on the surface of the implants. They cannot prevent bacteria from forming on the surface after treatment. Moreover, they cannot prevent bacterial contamination that can arise during the implantation procedure.

Surface texturing is a technique that can be used to increase biocompatibility of medical implants. Known methods for manufacturing medical devices with textured surfaces can produce random patterns of structures or can produce structures that are of a size and dimension unsuitable for application to medical implant devices. A need remains for a long-lasting, reliable medical implant systems and methods to prevent formation of biofilms on implant devices.

SUMMARY

Embodiments of the invention are directed to a method of fabricating an antibacterial surface for medical implant devices. A non-limiting example method includes patterning a photoresist layer on a semiconductor substrate. The substrate is etched using, for example, reactive ion etching to generate a plurality of nanopillars. The photoresist layer is removed from the substrate. The plurality of nanopillars are coated with a biocompatible film. The above-described fabrication method can produce controlled patterns of nanopillars with dimensions that promote bactericidal activity.

In some embodiments of the present invention, each of the plurality of nanopillars has a top pillar diameter within a range from about 1 nanometer to about 200 nanometers, a bottom pillar within a range from about 1 nanometer to about 1 micrometer, and/or an average height within a range from about 100 nanometers to about 10 micrometers. Embodiments of the invention with one or more of these dimensions can have increased bactericidal activity relative to nanopillars of dimensions outside of one or more of these ranges.

In some embodiments of the present invention, the biocompatible film includes titanium. Titanium and compounds containing titanium can provide a film with relatively low cost, relatively easy fabrication, and desirable bactericidal activity.

Embodiments of the invention are directed to a method of fabricating a medical implant device. A non-limiting example of the method includes generating a thin film including a plurality of nanostructures. In some embodiments, generating a thin film having a plurality of nanostructures includes applying a tensile layer to the plurality of nanostructures to cause a fracture in the semiconductor substrate. Generating a thin film also includes separating the plurality of nanopillars from the substrate at the fracture in the substrate. The method of fabricating can provide a silicon film including an antibacterial surface that is flexible and can conform to a variety of surfaces, including the surface of a medical implant.

In accordance with another embodiment, a method of fabricating an antibacterial structure for a medical implant device includes patterning a photoresist layer on a semiconductor substrate. The method also includes depositing a metal layer on the structure. The method also includes removing the photoresist layer and a portion of the metal layer from the structure to create a patterned metal layer. The method also includes etching the substrate under the patterned metal layer to generate a plurality of nanopillars. The method also includes removing the patterned metal layer from the structure. The method of fabricating can produce controlled patterns of nanopillars with dimensions that promote bactericidal activity at a reduced cost and with reduced use of toxic chemicals.

In accordance with another embodiment, a system for preventing bacterial infection associated with medical implants includes a thin silicon film including a plurality of nanopillars. The system can prevent bacterial infection associated with medical implants and enable adherence of human cells to the surface.

In accordance with one or more embodiments of the present invention, each of the plurality of nanopillars has a top pillar diameter within a range from about 1 nanometer to about 200 nanometers. Each of the plurality of nanopillars has a bottom pillar diameter within a range from about 1 nanometer to about 1 micrometer. The plurality of nanopillars has an average height within a range from about 100 nanometers to about 10 micrometers. The plurality of nanopillars are spaced on the thin silicon film with an average pitch within a range from about 100 nanometers to about 2 micrometers.

In accordance with yet another embodiment, a method for preventing bacterial infection associated with medical implant procedures is provided. The method includes applying a silicon film to a medical implant device, wherein the silicon film includes a plurality of nanopillars and a silicon base. The method also includes implanting the medical implant device in a patient. The method can prevent bacterial infection post-implantation and, thereby, improve patient outcomes.

BRIEF DESCRIPTION OF THE DRAWINGS

The foregoing and other features and advantages of the one or more embodiments described herein are apparent from the following detailed description taken in conjunction with the accompanying drawings in which:

FIGS. 2A-2D illustrate an exemplary fabrication process of forming an antibacterial surface for medical implant devices according to one or more embodiments of the present invention, in which:

FIG. 2A is a cross-sectional view of a silicon substrate after patterning a photoresist layer;

FIG. 2B is a cross-sectional view of the structure of FIG. 2A after etching;

FIG. 2C is a cross-sectional view of the structure of FIG. 2B after removing the photoresist layer; and FIG. 2D is a cross-sectional view of the structure of FIG. 2C after depositing a biocompatible material.

FIGS. 3A-3F illustrate another exemplary fabrication process of forming an antibacterial surface for medical implant devices according to one or more embodiments of the present invention, in which:

FIG. 3A is a cross-sectional view of a silicon substrate after patterning a photoresist layer;

FIG. 3B is a cross-sectional view of the structure of FIG. 3A after depositing a metal;

FIG. 3C is a cross-sectional view of the structure of FIG. 3B after removing the photoresist layer;

FIG. 3D is a cross-sectional view of the structure of FIG. 3C after conducting metal assisted chemical etching;

FIG. 3E is a cross-sectional view of the structure of FIG. 3D after removing the metal; and FIG. 3F is a cross-sectional view of the structure of FIG. 3E after depositing a biocompatible material.

FIGS. 4A-4D illustrate a process for forming a thinned down silicon structure including antibacterial nanopillars using a spalling technique, in which:

FIG. 4A is a cross sectional view of a substrate including antibacterial nanopillars;

FIG. 4B is a cross-sectional view of a silicon structure after deposition of a layer with tensile stress on a substrate;

FIG. 4C is a cross-sectional view of a silicon structure after deposition of a flexible handle on the layer with tensile stress; and FIG. 4D is a cross-sectional view of a silicon structure after lifting the layer with tensile stress to create a thin silicon ribbon including antibacterial nanopillars.

DETAILED DESCRIPTION

Figure 1:
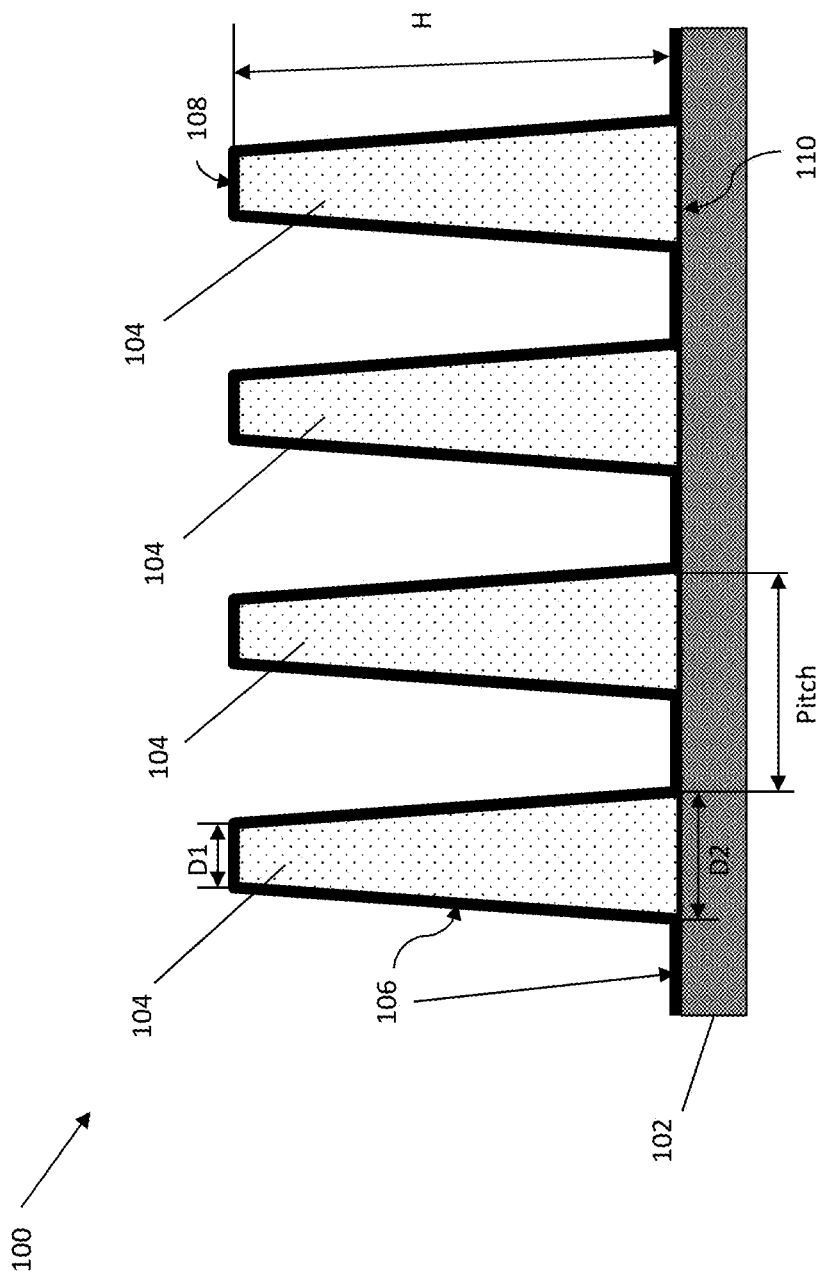
FIG. 1 is a cross-sectional view of an antibacterial surface for medical implant devices according to one or more embodiments of the present invention.

Medical implant devices are becoming more prevalent with the advent of new technologies for treatment of ailments associated with disease and aging. However, complete sterilization of the implanted devices through conventional means is difficult, resulting in the introduction of infectious materials into the body along with a surface that can provide a bacterial substrate for the formation of a biofilm. Such biofilms can not only result in potentially serious infections and illness, but also frequently require surgical intervention to remove the infectious material from the body. In addition, growth of bacterial films on the surface of implanted medical devices, including for instance pacemakers and orthopedic implants, can also block proper operation of the devices, sometimes leading to device malfunction.

There is a need to reduce or eliminate bacterial infection associated with medical devices to improve patient outcomes. Special considerations, such as biocompatibility, can be needed to prevent infections. Conventional methods for reducing such infections can include increasingly aggressive sterilization procedures, such as alpha radiation and high temperature steam heating. However, such methods are directed primarily to eliminating the presence of contaminants on the medical device prior to implantation and do not address other methods of contamination, such as during surgery, or bacterial growth after contamination.

Although propagation of bacterial cells on an implant surface is highly undesirable, some medical implant applications can benefit from attachment and propagation of human tissue on the implant surface. For example, adherence of muscle tissue to structural orthopedic implants can improve device functionality. In some cases, failure of muscle tissue to adhere to implanted medical devices can result in such poor prognosis that repeated surgical procedures are necessary.

Embodiments of the present invention include medical implant devices with anti-bacterial surfaces. Some embodiments of the invention provide methods of preventing bacterial film formation on medical implants. Embodiments of the present invention can provide medical implant devices that allow human cell adherence or growth on the device surface while prohibiting bacterial cell growth. In some embodiments of the present invention, patient treatment outcomes are improved, for instance by reducing risk of infection and subsequent surgical procedures. In addition, in some embodiments, the invention improves the functioning and longevity of medical implant devices.

Embodiments of the invention include a nanostructured surface for medical implant devices. In some embodiments, the nanostructured surface can be coated with bio-compatible materials. In some embodiments, the nanostructured surfaces of the invention prevent bacterial film formation. In some embodiments, the nanostructured surfaces of the invention allow growth of human cells. In some embodiments of the invention, nanopillar surfaces with controlled dimensions are provided. Fabrication of nanopillar surfaces with controlled dimensions can provide enhanced bactericidal activity in comparison with randomly ordered nanopillar surfaces.

Embodiments of the invention include improved methods of nanopillar surface formation. Methods according to some embodiments of the present invention provide nanopillar spikes with relatively small dimensions, providing enhanced bactericidal activity in comparison with nanopillars of larger dimensions.

Deposition is any process that grows, coats, or otherwise transfers a material onto a substrate. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes deep ultra violet lithography, electron-beam lithography, nanoimprint lithography, nanosphere lithography, and reactive ion etching.

The etching process can include a dry etch (e.g., reactive ion etching, plasma etching, ion beam etching, or laser ablation). The etching process can alternatively include a wet chemical etch (e.g., with potassium hydroxide, or sulfuric acid and hydrogen peroxide). In some exemplary embodiments, both dry etching and wet chemical etching processes can be used. After transferring the pattern, the patterned photoresist is removed utilizing resist stripping processes, for example, ashing. Ashing can be used to remove a photoresist material, amorphous carbon, or organic planarization (OPL) layer. Ashing is performed using a suitable reaction gas, for example, O2, N2, H2/N2, O3, CF4, or any combination thereof.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

Turning now to a more detailed description of embodiments of the present invention, FIG. 1 is a cross-sectional view of an antibacterial surface 100 for medical implant devices according to one or more embodiments of the present invention. The antibacterial surface 100 can include a semiconductor substrate 102, such as a silicon substrate, and a plurality of nanopillars 104. In some embodiments, the substrate 102 and nanopillars 104 are formed of the same material and include silicon or a silicon compound. Each nanopillar includes a top surface 108. The top surface 108 of each nanopillar has a top diameter D1. The bottom of each nanopillar at its widest point has a bottom diameter D2. The nanopillars each have a height H. In some embodiments, the nanopillars 104 are spaced from each other of a distance defined by a pitch. The pitch is the distance from a leading edge of a first nanopillar to the leading edge of a second nanopillar, where the second nanopillar is the next neighboring nanopillar on the substrate 102. In some embodiments, the substrate 102 and nanopillars 104 are optionally coated with a bio-compatible film 106.

In some embodiments, one or more nanopillars has a top pillar diameter D1 that is within a range from about 1 nanometer (nm) to about 200 nm. In some embodiments, D1 is within a range from about 1 nm to about 150 nm, such as from about 1 nm to about 100 nm, or from about 10 nm to about 80 nm. In some embodiments, the average diameter on the antibacterial surface D1 is about 50 nm to about 80 nm.

In some embodiments, one or more nanopillars has a bottom pillar diameter D2 that is within a range from about 1 nm to about 1000 nm. In some embodiments, D2 is from about 50 nm to about 500 nm, such as from about 100 nm to about 400 nm, or from about 100 nm to about 200 nm. In some embodiments, the average diameter D2 of the nanopillars on the antibacterial surface 100 is within a range from about 100 nm to about 150 nm.

In some embodiments, plurality of nanopillars are spaced on the substrate according to a pitch. In some embodiments, the average pitch of the nanopillars 104 on the antibacterial surface 100 is within a range from about 100 nm to about 2 micrometers (µm). In some embodiments the average pitch is within a range from about 100 nm to about 1000 nm, such as from about 100 nm to about 500 nm, or from about 200 nm to about 500 nm. In some embodiments, the average pitch is within a range from about 400 nm to about 450 nm.

In some embodiments, one or more nanopillars has a height H of the nanopillars H is within a range from about 100 nm to about 10 µm. In some embodiments, the height is within a range from about 100 nm to about 1 µm, or from about 200 nm to about 800 nm, or from about 300 nm to about 700 nm, or from about 400 nm to about 600 nm. In some embodiments, the average height of the nanopillars 104 on the antibacterial surface 100 is within a range from about 400 nm to about 500 nm.

Biocompatible film 106 is a layer including a bio-compatible material that can be applied to the nanopillars and substrate of an antibacterial surface. Biocompatible film 106 can include, for instance, nitrides, oxides, including metallic oxides, metallic hydroxides, nanoporous inorganic coatings, such as hydroxyapatite and calcium phosphate compounds, and polymers, including natural polymers and synthetic polymers. In some embodiments, biocompatible film 106 includes, for example, aluminum oxide, hydroxyapatite, silicon dioxide, titanium carbide, titanium nitride, titanium dioxide, zirconium dioxide, calcium phosphate, chromium nitride, collagen, chitosan, cellulose or cellulose derivatives, poly-/-lactic acid (PLLA), poly(ε-caprolactone) (PCL), poly (lactide-co-glycolide) (PLGA), poly(ether imide) (PEI), poly(1,3-trimethylene carbonate) (PTMC), poly(styrene sulfonate) (PSS), or combinations thereof. In some embodiments of the invention, biocompatible film 106 includes a conductive metal, including, but not limited to, platinum, silver, aluminum, nickel, titanium, or alloys thereof. In some embodiments, the biocompatible layer 106 is composed of titanium (Ti). In some embodiments, the biocompatible layer 106 is composed of titanium nitride (TiN).

Figure 2A:
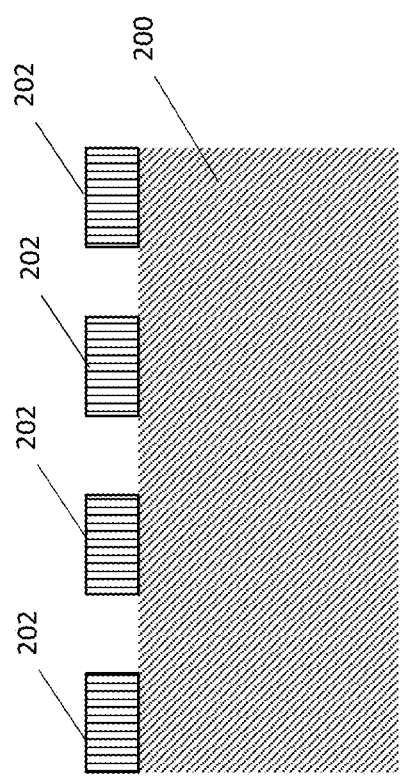

FIGS. 2A-2D illustrate an exemplary fabrication process of forming an antibacterial surface for medical implant devices according to one or more embodiments of the present invention. FIG. 2A is a cross-sectional view of a silicon substrate 200 after patterning a photoresist layer 202. As is shown in FIG. 2A, a silicon substrate 200 can be provided and a photoresist layer 202 can be patterned on the substrate 200, leaving the substrate 200 exposed for subsequent etching and nanopillar formation. The photoresist layer can be patterned with any suitable nanolithography technique, such as electron-beam lithography, deep ultra violet (UV) photolithography, nanosphere lithography, or nanoimprint technology.

Figure 2B:
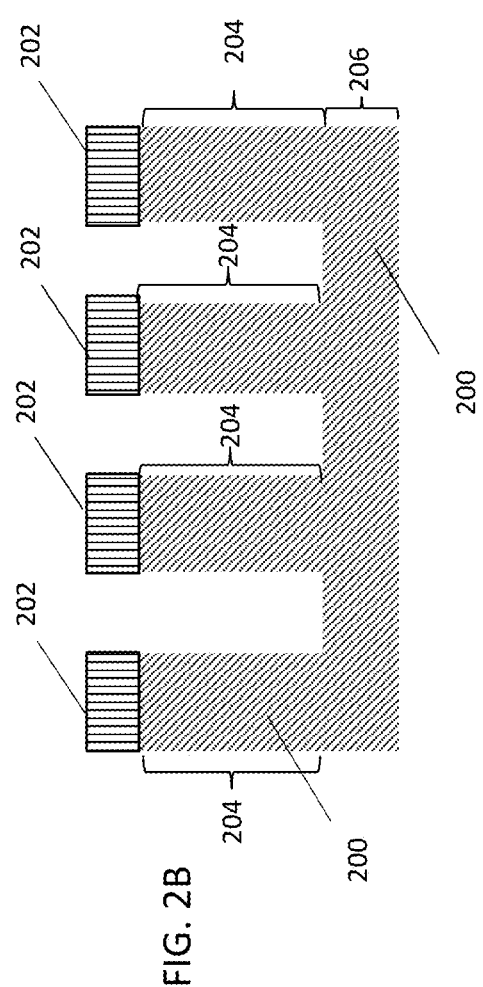

FIG. 2B is a cross-sectional view of the structure of FIG. 2A after etching. The exposed or unmasked regions of the silicon substrate 200 can be etched, for example, with reactive ion etching (ME) to a desired depth. The desired depth can depend upon the desired height of the resultant nanopillars. Etching can result in a plurality of nanopillars 204 on a silicon base 206. The nanopillars 204 and silicon base 206 can be formed of the silicon substrate 200. Each of the nanopillars 204 can be capped by the photoresist layer 202.

Figure 2C:
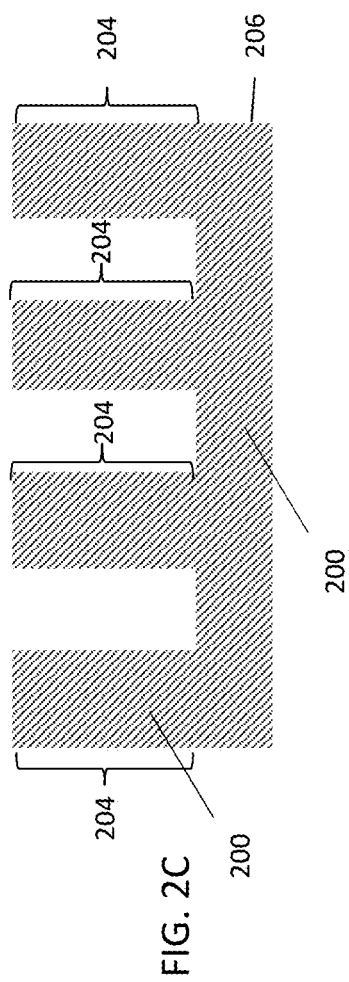

After etching the silicon substrate 200, the photoresist layer 202 can be removed from the structure by known techniques. FIG. 2C is a cross-sectional view of the structure of FIG. 2B after removing the photoresist layer. The resultant structure can include a plurality of nanopillars 204 and silicon base 206, each formed of the silicon substrate 200, having the desired dimensions.

Figure 2D:
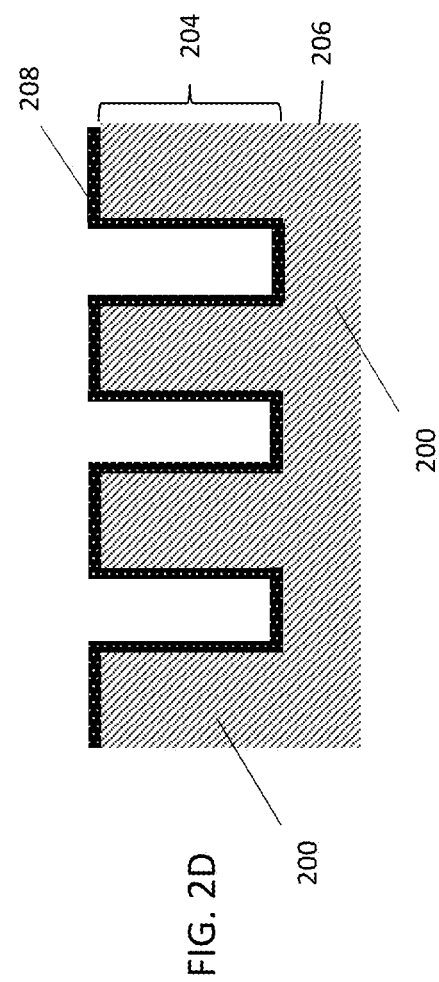

In some embodiments, after removing the photoresist layer, the structure can be coated with a layer of biocompatible film 208. FIG. 2D is a cross-sectional view of the structure of FIG. 2C after depositing a biocompatible film 208. The biocompatible film 208 can be deposited by known methods, for instance, by chemical vapor deposition (CVD) or atomic layer deposition (ALD). In some embodiments of the present invention, biocompatible film 208 is deposited utilizing a method which forms a conformal coating on the exposed surfaces of substrate 200, including the exposed surfaces of features 204 and 206.

Figure 3A:
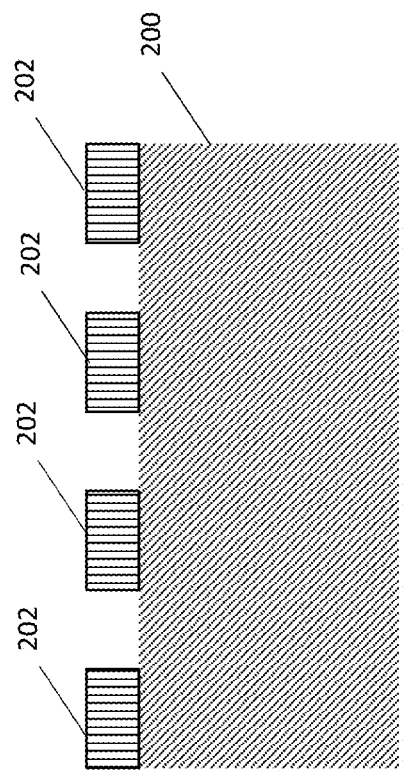

FIGS. 3A-3F illustrate another exemplary fabrication process of forming an antibacterial surface for medical implant devices according to one or more embodiments of the present invention. The process can include patterning a photoresist layer 202 on a silicon substrate 200. FIG. 3A is a cross-sectional view of a silicon substrate after patterning a photoresist layer 202.

Figure 3B:
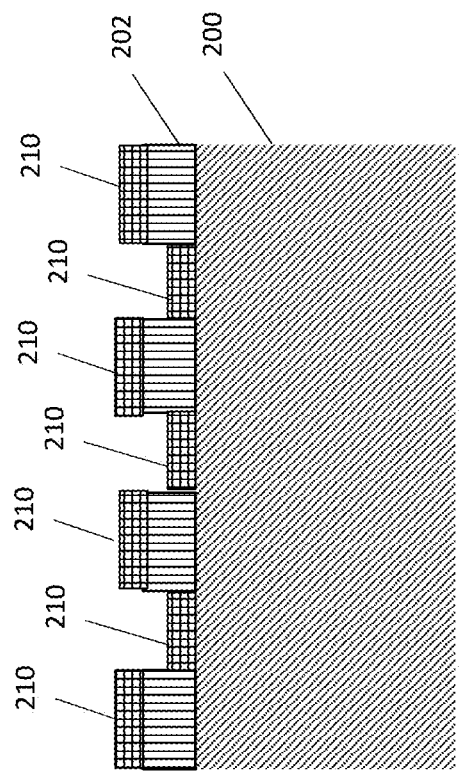

After patterning a photoresist layer, metal-assisted chemical etching can be performed to create a plurality of nanopillars according to one or more embodiments of the present invention. FIG. 3B is a cross-sectional view of the structure of FIG. 3A after depositing a metal layer 210. As is illustrated a metal layer 210 can be deposited on the structure on top of the photoresist layer 202 and the exposed regions of the silicon substrate 200.

The metal layer 210 can include any metal suitable for metal-assisted chemical etching, such as gold, silver, platinum, tungsten, palladium, copper, aluminum, titanium, nickel, iron, zinc, cadmium, indium, tin, antimony, tellurium, lead, bismuth, vanadium, chromium, manganese, ruthenium, or molybdenum. In some embodiments, the metal 210 includes gold.

Figure 3C:
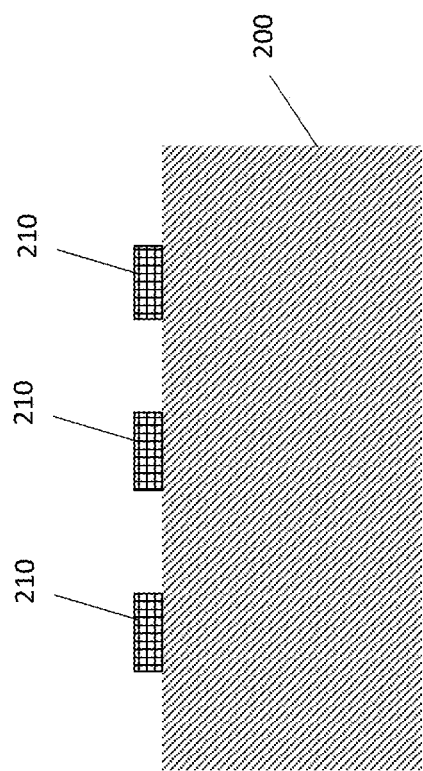

After depositing the metal layer 210 on the structure, the photoresist layer and associated metal can be removed from the structure, leaving metal layer 210 in a pattern suitable for producing nanopillars of the desired dimensions. FIG. 3C is a cross-sectional view of the structure of FIG. 3B illustrating a silicon substrate 200 and patterned metal layer 210 after removing the photoresist layer.

Figure 3D:
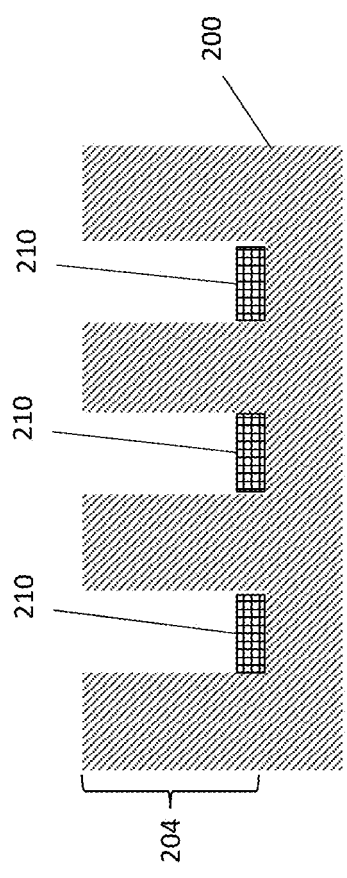

FIG. 3D is a cross-sectional view of the structure of FIG. 3C after conducting metal assisted chemical etching. Methods and etchants suitable for metal-assisted chemical etching (MacEtch) are known. For example, the silicon 200 under the metal 210 can be etched with fluoride etchant, such as hydrofluoric acid, and an oxidizing agent, such as hydrogen peroxide. MacEtch can include, for example, inducing local oxidation and reduction reactions with noble metals, such as gold or platinum, deposited on the surface of a semiconductor material. Such reactions can be locally restricted to the interface between metal and semiconductor. MacEtch can be a desirable alternative to reactive ion etching, for example, because it can be less costly than reactive ion etch procedures and can, in some cases, consume less energy, and in some cases also reduce exposure and handling of toxic materials.

Figure 3E:
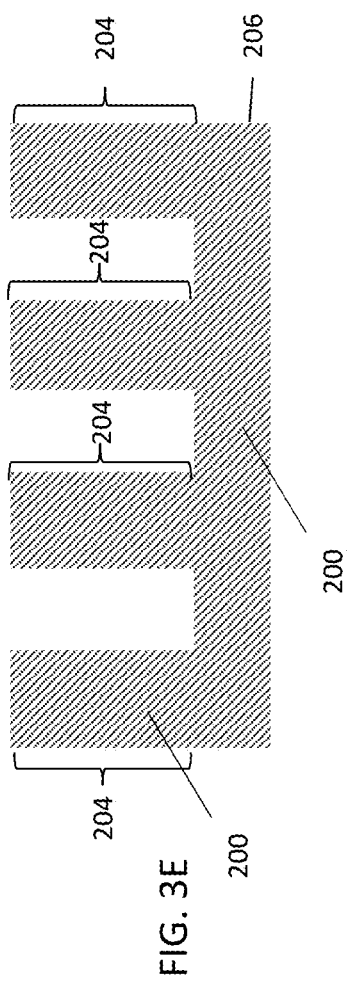

According to some embodiments of the present invention, after etching, the metal can be removed from the structure. FIG. 3E is a cross-sectional view of the structure of FIG. 3D after removing the patterned metal layer. As is illustrated, nanopillars 204 can be formed from the substrate 200 with desired dimensions.

Figure 3F:
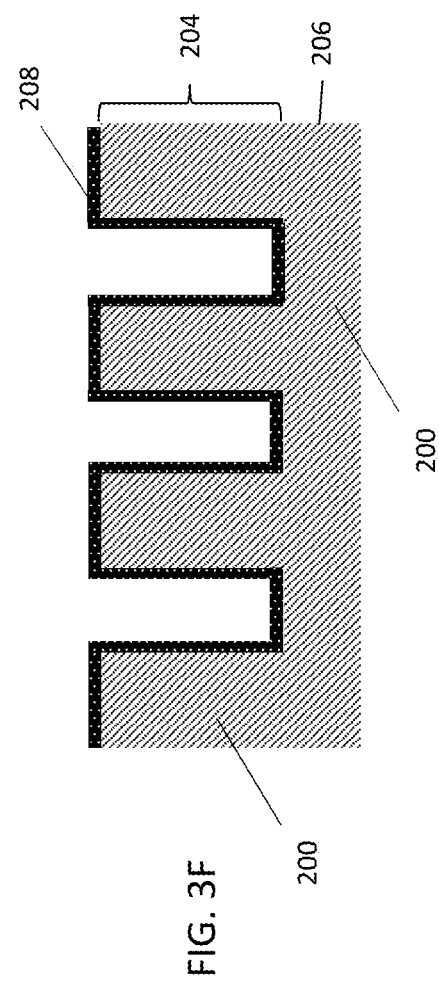

In some embodiments, after removing the metal, a biocompatible film can be deposited on the structure. FIG. 3F is a cross-sectional view of the structure of FIG. 3E after depositing a biocompatible film 208.

Figure 4A:
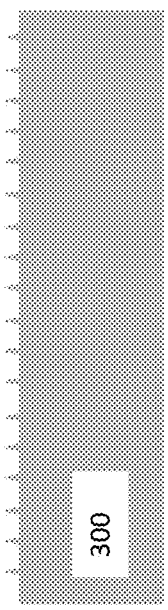
Figure 4B:
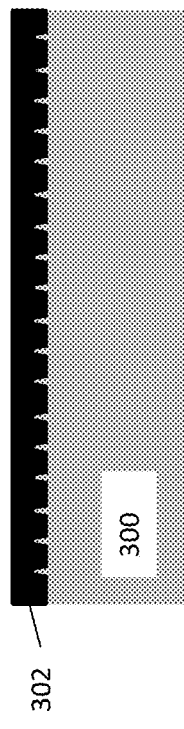

For example, FIGS. 4A-4D illustrate one known process for forming a thinned down silicon structure including antibacterial nanopillars using a controlled spalling technique. As shown in FIG. 4A, a silicon structure including antibacterial nanopillars 300 is provided. As is shown in FIG. 4B, a layer with tensile stress 302 can be deposited on the structure 300. Layer with tensile stress, or tensile layer 302, can be a layer of metal under tensile strain, for instance tensile strained Ni. Tensile layer 302 can include any material useful for spalling a thin silicon ribbon from a silicon substrate, such as tensile stressed metal or metal alloy.

Figure 4C:
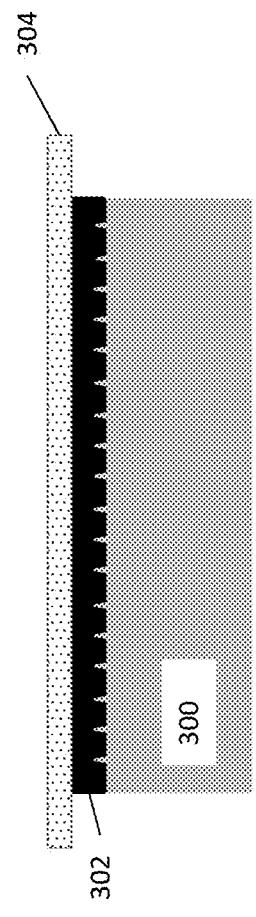
Figure 4D:
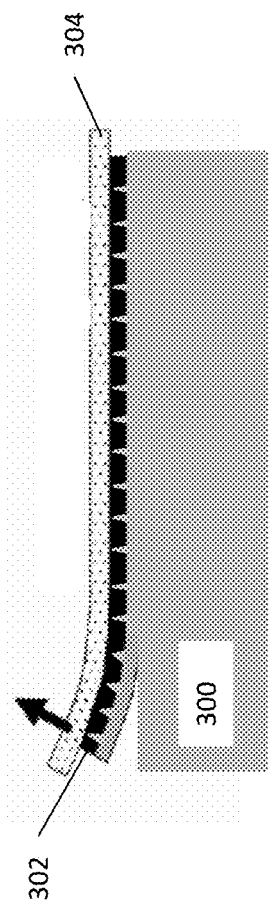

The tensile layer 302 can cause a fracture in the silicon structure 300. Next, as shown in FIG. 4C, a flexible handle layer 304 can be disposed on the tensile layer. The flexible handle 304 can include, for example a plastic or metal foil that is operatively associated with, i.e., glued, adhered, or bonded to the tensile layer. Then, as shown in FIG. 4D, a known spalling technique can include lifting the tensile layer 302 by means of the attached flexible handle 304 separate the plurality of nanopillars from the silicon substrate at the fracture on the silicon substrate to create a thin layer of silicon ribbon including antibacterial nanopillars from substrate 300.

In some embodiments of the present invention, the thin silicon ribbon including antibacterial nanopillars has a thickness within a range from about 1 microns to about 100 microns. In some embodiments of the present invention, the thin silicon ribbon including antibacterial nanopillars has a thickness of less than 50 microns.

The descriptions of the various embodiments of the present invention have been presented for purposes of illustration, but are not intended to be exhaustive or limited to the embodiments described herein. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:
1. A system for preventing bacterial infection associated with medical implant procedures, comprising:
a silicon film comprising a controlled pattern of a plurality of nanopillars that have been etched into a silicon base, the plurality of nanopillars spaced apart at regular intervals comprising a pitch of 400 to 450 nm, the plurality of nanopillars formed by:
patterning a photoresist to expose a surface of the silicon base;
depositing a metal layer on a top surface of the photoresist and on the exposed surface of the silicon base;
removing the photoresist to lift off portions of the metal layer on the top surface of the photoresist; and
recessing portions of the silicon base under remaining portions of the metal layer using a metal-assisted chemical etch, wherein the metal-assisted chemical etch is locally restricted to an interface between the remaining portions of the metal layer and the exposed surface of the silicon base;

wherein each of the plurality of nanopillars has a top pillar diameter within a range from about 1 nanometer to about 200 nanometers; and wherein each of the plurality of nanopillars has a same height.

2. The system according to claim 1, further comprising a biocompatible film.

3. The system according to claim 2, wherein the biocompatible film coats a surface of the plurality of nanopillars.

4. The system according to claim 2, wherein the biocompatible film comprises titanium.

5. The system according to claim 2, wherein the biocompatible film forms a conformal coating on the plurality of nanopillars.

6. The system according to claim 2, wherein the biocompatible film comprises a conductive metal.

7. The system according to claim 6, wherein the conductive metal film comprises platinum, silver, aluminum, nickel, titanium, or alloys thereof.

8. The system according to claim 2, wherein the biocompatible film comprises aluminum oxide, hydroxyapatite, silicon dioxide, titanium carbide, titanium nitride, titanium dioxide, zirconium dioxide, calcium phosphate, chromium nitride, collagen, chitosan, cellulose or cellulose derivatives, poly-/-lactic acid (PLLA), poly(ε-caprolactone) (PCL), poly(lactide-co-glycolide) (PLGA), poly(ether imide) (PEI), poly(1,3-trimethylene carbonate) (PTMC), poly(styrene sulfonate) (PSS), or combinations thereof.

9. The system according to claim 2, wherein the biocompatible film comprises nitrides, oxides, metallic oxides, metallic hydroxides, nanoporous inorganic coatings, natural polymers, synthetic polymers, or a combinations thereof.

10. The system according to claim 2, wherein the biocompatible film comprises titanium nitride.

11. The system according to claim 1, wherein the silicon base has a thickness of less than or equal to about 100 micrometers.

12. The system according to claim 1, wherein the silicon film has a thickness of about 1 micron to about 100 microns.

13. The system according to claim 1, wherein the silicon film is flexible.

14. The system according to claim 1, wherein the silicon film is adhered to a surface of a medical implant device.

15. The system according to claim 14, wherein the medical implant device allows human cell adherence or growth.

16. The system according to claim 1, wherein the silicon film has a thickness of less than 50 micrometers.

* * * * *